(12) United States Patent
Kudo et al.

(10) Patent No.: US 9,284,338 B2
(45) Date of Patent: Mar. 15, 2016

(54) SILICONE COMPOUND AND A USE THEREOF (71) Applicant: SHIN-ETSU CHEMICAL CO., LTD., Tokyo (JP)

(72) Inventors: Muneo Kudo, Annaka (JP); Shoji Ichinohe, Annaka (JP); Tomoyuki Goto, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/729,778

(22) Filed: Jun. 3, 2015

(65) Prior Publication Data

US 2015/0361113 A1 Dec. 17, 2015

(30) Foreign Application Priority Data

Jun. 12, 2014 (JP) .................................. 2014-121223

(51) Int. Cl.
*C07F 7/00* (2006.01)
*C07F 7/08* (2006.01)
(Continued)

(52) U.S. Cl.
CPC ............. *C07F 7/0854* (2013.01); *C07F 7/0889* (2013.01); *C08F 220/36* (2013.01); *G02B 1/043* (2013.01)

(58) Field of Classification Search
None
See application file for complete search history.

(56) References Cited

U.S. PATENT DOCUMENTS 4,543,398 A * 9/1985 Bany ........................ C08F 30/08
351/159.33
4,709,066 A * 11/1987 Chapman ................ C07F 7/025
526/279

(Continued)

FOREIGN PATENT DOCUMENTS

EP 1 818 692 A2 8/2007
JP S59-78236 A 5/1984
(Continued)

OTHER PUBLICATIONS

Sep. 25, 2015 Extended Search Report issued in European Patent Application No. 15171250.2.

*Primary Examiner* — Robert S Loewe
(74) *Attorney, Agent, or Firm* — Oliff PLC (57) ABSTRACT

One of the purposes of the present invention is to provide a compound which is a polymerizable monomer having a specific number of silicon atoms and a specific number of fluorine atoms, has a higher purity, is suitable as an ophthalmic monomer, is well compatible with another (meth)acryl monomer, and provides a polymer having excellent hydrophilicity, anti-staining property and durability of mechanical strength and to provide a method for preparing the compound. The present invention provides a compound represented by the following formula (1).

Further, the present invention provides a method for preparing the compound, a polymer having repeating units derived from the aforesaid compound and an ophthalmic device composed of the polymer.

16 Claims, 1 Drawing Sheet

(51) Int. Cl.
*C08F 220/36* (2006.01)
*G02B 1/04* (2006.01)

(56) References Cited

U.S. PATENT DOCUMENTS

| | | | |
|---|---|---|---|
| 5,321,108 A * | 6/1994 | Kunzler | C08F 30/08 523/107 |
| 5,908,906 A * | 6/1999 | Kunzler | C07F 7/085 351/159.19 |
| 6,043,328 A | 3/2000 | Domschke et al. | |
| 6,310,169 B1 * | 10/2001 | Kawabata | C08G 77/38 525/474 |
| 2002/0016383 A1 * | 2/2002 | Iwata | B29D 11/00125 351/159.04 |
| 2002/0107337 A1 | 8/2002 | Rosenzweig et al. | |
| 2004/0198938 A1 * | 10/2004 | Nakamura | C07F 7/0852 526/279 |
| 2004/0201820 A1 * | 10/2004 | Nakamura | G02B 1/043 351/159.01 |
| 2004/0249180 A1 * | 12/2004 | Nakamura | C07F 7/0852 556/443 |
| 2008/0269429 A1 | 10/2008 | Arkles et al. | |
| 2009/0299022 A1 | 12/2009 | Ichinohe | |
| 2012/0184696 A1 | 7/2012 | Broad et al. | |
| 2012/0220689 A1 * | 8/2012 | Yao | G02B 1/043 523/107 |

FOREIGN PATENT DOCUMENTS

| | | |
|---|---|---|
| JP | 2001-055446 A | 2/2001 |
| JP | 2003-516562 A | 5/2003 |
| JP | 2007-001918 A | 1/2007 |
| JP | 2007-186709 A | 7/2007 |
| JP | 2008-274278 A | 11/2008 |
| JP | 4646152 B2 | 3/2011 |
| JP | 4882136 B2 | 2/2012 |
| JP | 2013-507652 A | 3/2013 |
| WO | 96/31791 A1 | 10/1996 |
| WO | 01/42846 A1 | 6/2001 |
| WO | 2011/045299 A1 | 4/2011 |

* cited by examiner

SILICONE COMPOUND AND A USE THEREOF

CROSS REFERENCE

This application claims the benefits of Japanese Patent Application No. 2014-121223 filed on Jun. 12, 2014, the contents of which are hereby incorporated by reference.

FIELD OF THE INVENTION

The present invention relates to a compound which is useful as starting materials for preparing ophthalmic devices such as contact lenses, intraocular lenses and artificial corneas, hereinafter also referred to as ophthalmic monomer, and a method for the preparation thereof. Specifically, the present invention relates to a compound which has a specific number of silicone atoms and a specific number of fluorine atoms, is copolymerizable with the other polymerizable monomer such as a (meth)acryl monomer to provide a polymer having high transparency and oxygen permeability, excellent hydrophilicity, anti-staining property and durability of mechanical strength and being suitable for ophthalmic uses, and a method for preparing the silicone compound.

The following silicone compounds are known as an ophthalmic monomer.

The afore-mentioned TRIS, 3-[tris(trimethylsiloxy)silyl] propyl methacrylate, has poor compatibility with hydrophilic monomers such as 2-hydroxyethylmethacrylate (HEMA). Therefore, when TRIS is copolymerized with a hydrophilic monomer, there is such a disadvantage that a transparent polymer is not obtained. In contrast, SiGMA described above has good compatibility with hydrophilic monomers such as HEMA. The copolymers obtained from SIGMA have relatively high oxygen permeability and high hydrophilicity. Recently, higher oxygen permeability is required for an ophthalmic polymer so as to be used continuously on eyes for a longer term. Polymers obtained from SIGMA do not have sufficient oxygen permeability.

In order to solve this problem, Japanese Patent Application Laid-Open No. 2007-186709, Patent Literature 1, describes a compound represented by the following formula (a).

In the afore-mentioned SiGMA, the weight ratio of the Si-containing moiety, i.e. bis(trimethylsiloxy)methylsilyl, to the whole molecule is 52%. In contrast, in the aforesaid formula (a), the weight ratio of the Si-containing moiety, i.e. tris (trimethylsiloxy)silyl, to the whole molecule is 60%. The compound represented by the formula (a) thus has the higher weight ratio of the Si-containing moiety and, therefore, gives higher oxygen permeability to ophthalmic devices.

However, there is a problem such that when the weight ratio of the Si-containing moiety is increased in order to improve oxygen permeability, the mole weight of the polymerizable group became large and, therefore, strength of the copolymer deteriorated. Japanese Patent Application Laid-Open No. 2007-1918, Patent Literature 2, describes that the compound represented by the aforesaid formula (a) is prepared by a reaction of a corresponding epoxy precursor and methacrylic acid. There is such a problem such that many side reactions occur and the physical properties of the resulting copolymers vary.

Japanese Patent No. 4882136, Paten Literature 3, describes a compound represented by the following formula (e) and an ophthalmic lens prepared from a polymer having repeating units derived from the compound.

However, the polymer obtained by polymerization using the aforesaid compound as a monomer component has poor mechanical strength, and a reactivity of the polymerization of the compound is poor. Further, a anti-staining property of the polymer obtained is insufficient. Patent Literature 3, claim 3, also describes a monomer having a urethane bond. However, this monomer has such a siloxane structure as tris(trimethylsiloxy) silyl, bis(trimethylsiloxy)methylsilyl and pentamethyldisiloxane, and does not has a chain siloxane structure. A polymer obtained from a monomer of this structure may have lower oxygen permeability or a bad shape recovery property.

It is known that a silicone having a tetrameric or more structure is thought to be preferable in term of oxygen permeability and, in particular, a silicone having a tetrameric or pentameric structure is thought to be more preferable in order to balance between oxygen permeability and strength of the copolymer. Therefore, development of a method for preparing a silicone monomer having a tetrameric or more structure with a high purity is desired.

Japanese Patent Application Laid-Open No. Sho 59-78236, Patent Literature 4, describes a method for the preparation of a silicone compound represented by a following formula (b), comprising steps of anion-polymerizing a cyclic siloxane in the presence of a lithium trialkylsilanolate as an initiator and, then, reacting the reaction product with a chlorosilane having a (meth)acryl group, such as 3-(2-methacryloyloxy ethoxy) propyl dimethyl chlorosilane.

However, when the silicone compound obtained in the aforementioned method is mixed with a hydrophilic monomer, such as 2-hydroxyethyl methacrylate, turbidity occurs sometimes. Further, a ratio of terminals of the silicone chain blocked with the chlorosilane is not high.

Japanese Patent Application Laid-Open No. 2001-55446, Patent Literature 5, describes a method for preparing a silicone compound represented by the following formula (c) by esterifying (meth)acrylic acid or transesterifying (meth)acrylate with an organopolysiloxane having a hydroxyl group at the one terminal, wherein r is an integer of 3 or larger.

However, the esterification ratio is insufficient, the blocked terminal ratio is low, and the compound has broad distribution of a polymerization degree of the silicone moiety.

Japanese Patent No. 4646152, Patent Literature 6, describes a method for preparing a silicone monomer represented by the following formula (d) by esterifying an organopolysiloxane having a hydroxyl group at the one terminal and a (meth)acrylic acid halide:

wherein m is one value out of the integers of from 3 to 10, n is one value out of 1 and 2, $R^1$ is only one out of alkyl groups having 1 to 4 carbon atoms, and $R^2$ is only one out of a hydrogen atom and a methyl group, and more than 95 weight % of the compound is one kind of compound having the specific one structure, i.e., each one value of m, n, $R^1$ and $R^2$.

A monomeric compound having a fluorinated hydrocarbon group was developed in order to increase oxygen permeability of its polymer or add anti-staining property to its polymer. For instance, Japanese National Phase Publication No. 2003-516562 describes a method for copolymerizing a hydrophilic monomer, a monomer having tris(siloxysilyl) group and a monomer having a fluorinated hydrocarbon group.

Japanese Patent Application Laid-Open No. 2008-274278 and Japanese National Phase Publication No. 2013-507652 describe a fluorine-containing silicone monomer having a siloxane chain to which a fluorinated hydrocarbon group bonds as a side chain and a polymerizable group, represented by the following formula.

wherein X is a polymerizable group, $R_1$ is, independently of each other, an alkyl group having 1 to 6 carbon atoms or —$R_4$—$CF_3$, wherein $R_4$ is, independently of each other, an alkenyl group having 1 to 6 carbon atoms, $R_2$ is, independently of each other, an alkenyl group having 1 to 6 carbon atoms or a fluorine-containing alkenyl group having 1 to 6 carbon atoms, $R_3$ is a group selected from the group consisting of a monovalent linear or branched alkyl group, a siloxane chain having 1 to 30 Si—O units, a phenyl group, a benzyl group, a linear or branched hetero atom-containing group, or a combination of these, m is 1 to 6, n is 0 to 14, p is 1 to 14, a total of n and p is 15 or less, Y is a divalent connecting group, a is 0 or 1, q is 1 to 3, r is 3-q.

PRIOR LITERATURES

Patent Literature 1: Japanese Patent Application Laid-Open No. 2007-186709
Patent Literature 2: Japanese Patent Application Laid-Open No. 2007-1918
Patent Literature 3: Japanese Patent No. 4882136
Patent Literature 4: Japanese Patent Application Laid-Open No. Sho 59-78236
Patent Literature 5: Japanese Patent Application Laid-Open No. 2001-55446
Patent Literature 6: Japanese Patent No. 4646152
Patent Literature 7: Japanese National Phase Publication No. 2003-516562
Patent Literature 8: Japanese Patent Application Laid-Open No. 2008-274278
Patent Literature 9: Japanese National Phase Publication No. 2013-507652

SUMMARY OF THE INVENTION

The polymers obtained from the monomer compounds described in Patent Literatures 3 and 6 have poor durability of mechanical strength so that the mechanical strength may deteriorate in a phosphate buffer solution. The monomers described in Patent Literature 7 are less compatible with each other and the polymer obtained becomes cloudy and cause microphase separation. Further, the monomer described in Patent Literatures 8 and 9 does not have a hydrophilic group at a part bonding the (meth)acryl group and the siloxanyl group, so that the monomer is less compatible with hydrophilic monomers.

Further, Patent Literatures 8 and 9 describe that the aforesaid compound is prepared by subjecting a fluorinated hydrocarbon-containing cyclotrisiloxane to a living polymerization with alkyl lithium or lithium alkyl dimethyl silanolate as an initiator, and capping the terminal with methacryloxypropyl dimethyl chlorosilane after all of the cyclosiloxane monomer reacts. However, in the method, control of the number of siloxane repeating units having a fluorinated hydrocarbon group is difficult and, therefore, a product obtained is a mixture of compounds having various amounts of fluorine atoms. Further, the amount of fluorine atoms is too large, the compatibility between the compound and the other monomers is worse, a polymer obtained becomes cloudy and microphase separation occurs. Further, mechanical strength of a polymer obtained from the monomer may deteriorate in a phosphate buffer solution.

One of the purposes of the present invention is to provide a compound which is a polymerizable monomer having a specific number of silicon atoms and a specific number of fluorine atoms, has a higher purity, is suitable as an ophthalmic monomer, is well compatible with another (meth)acryl monomer, and provides a polymer having excellent hydrophilicity, anti-staining property and durability of mechanical strength and to provide a method for preparing the compound.

The present inventors have made research to solve the afore-mentioned problems and found that a compound represented by the following formula (1) is well compatible with other (meth)acryl monomers and provides a colorless and transparent polymer which has excellent hydrophilicity, anti-staining property and durability of mechanical strength.

Thus, the present invention provides a compound represented by the following formula (1):

(1)

wherein m is an integer of from 2 to 10, n is an integer of from 1 to 3, k is an integer of 1 or 2, $R^1$ is, independently of each other, an alkyl group having 1 to 6 carbon atoms, $R^2$ is, independently of each other, an alkylene group having 1 to 6 carbon atoms or a fluoroalkylene group having 1 to 6 carbon atoms, $R^3$ is an alkyl group having 1 to 4 carbon atoms, and $R^4$, $R^5$ and $R^6$ are, independently of each other, a hydrogen atom or a methyl group.

Further, the present invention provides a method for preparing the compound, use of the compound as an ophthalmic monomer, a polymer having repeating units derived from the aforesaid compound and an ophthalmic device composed of the polymer.

EFFECTS OF THE INVENTION

The present silicone compound has higher oxygen permeability, has one kind of specific structure at a high ratio, and is well compatible with other (meth)acryl monomers to thereby provide a colorless and transparent polymer. Further, the present compound has the specific amount of fluorine atoms to thereby provide a polymer having excellent anti-staining property. The present compound has the specific amount of silicon atoms to thereby have a higher oxygen permeability. Further, the compound has a urethane bond in a spacer moiety in the molecular and, therefore, the compound provides a polymer which forms hydrogen bonds between the other polymers and has excellent durability of mechanical strength. The mechanical strength of the polymer does not deteriorate in a phosphate buffer solution. Further, the compound has hydrophilic alkyleneoxide structures in the both sides of the urethane bond, so that the compound provides a polymer having excellent hydrophilicity. The present method comprises a reaction of a silicone compound having a hydroxyl group and a (meth)acryl group-containing isocyanate compound. The present method provides a compound having one kind of specific structure at a high ratio. Accordingly, the present compound and the present method are useful for preparing ophthalmic devices.

DETAILED DESCRIPTION OF THE INVENTION

Figure 1:
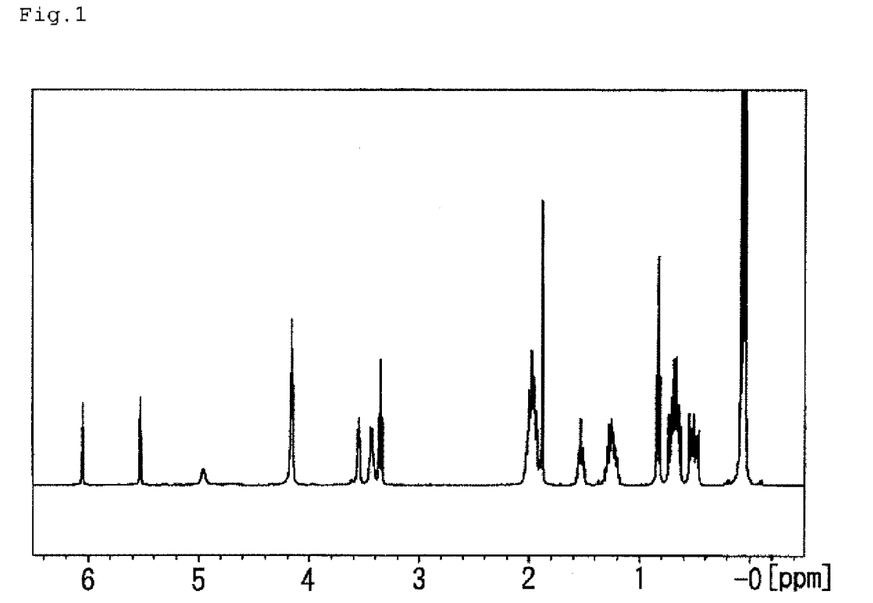
FIG. 1 is a chart of $^1$H-NMR spectra of the silicone compound prepared in Example 1.
Figure 2:
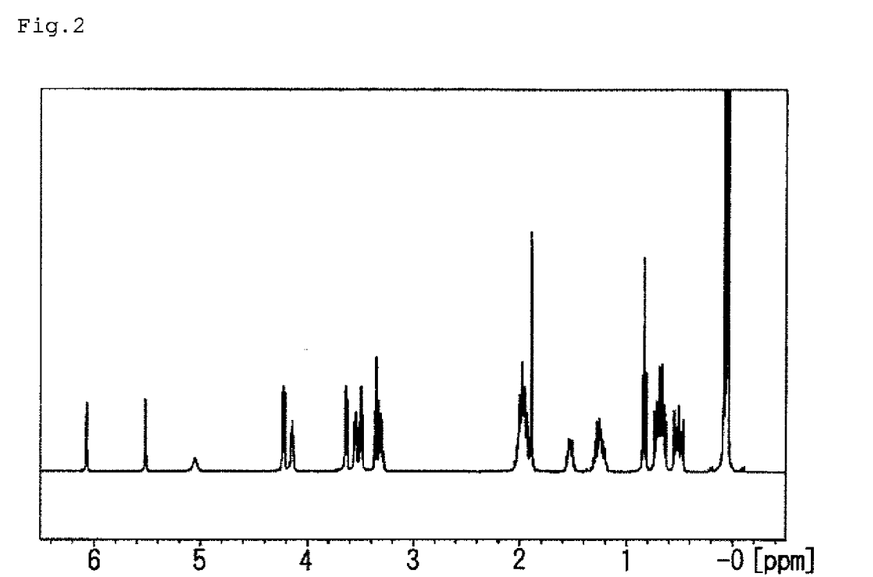
FIG. 2 is a chart of $^1$H-NMR spectra of the silicone compound prepared in Example 2.

The present silicone compound is represented by the aforesaid formula (1), and has a silicone chain structure having a fluorinated hydrocarbon side group, a urethane bond in a spacer structure bonding the silicone structure and the (meth)acryl structure, and alkyleneoxide structures in the both sides of the urethane bond. On account of the aforesaid specific structures, the present compound is well compatible with other polymerizable monomers and provides a colorless and transparent polymer having a higher oxygen permeability and increased hydrophilicity, anti-staining property and durability of mechanical strength.

In the aforesaid formula (1), m is an integer of from 2 to 10, preferably 3 to 7, more preferably 3. If m is smaller than the lower limit, the oxygen permeability of the polymer is worse. If m is larger than the upper limit, the hydrophilicity of the polymer is worse. When m is within the aforesaid limits, the compound has a linear siloxane structure having the desired amount of silicon atoms, so that a polymer obtained has good oxygen permeability and shape recovery property.

In the aforesaid formula (1), $R^5$ is, independently of each other, a hydrogen atom or a methyl group. n is an integer of from 1 to 3. The present compound has alkyleneoxide structures in the part bonding the urethane bond and the siloxane structure to thereby has the good hydrophilicity. If n is zero, the hydrophilicity is worse. If n is larger than 3, the compound does not have one kind of a specific structure at a high ratio and a polymer thereof has poor durability and mechanical strength. Preferably, n is 1 or 2 and the silicone compound preferably has an ethylene oxide structure, an ethylene oxide-ethylene oxide structure, an ethylene oxide-propylene oxide structure or a propylene oxide-ethylene oxide structure. According to the aforesaid structure, the compound has good balance of hydrophilicity. Particularly, preferred is the compound having an ethylene oxide structure whose n is 1 and $R^5$ is a hydrogen atom. If the compound has too many propylene oxide structures, the hydrophobicity of the polymer obtained is too high and the hydrophilicity is poorer.

In the aforesaid formula (1), k is an integer of 1 or 2. If k is 0, the hydrophilicity is poorer. If k is 3 or more, the hydrophilicity is too high, so that a high ratio of one specific structure of the formula (1) is not attained by washing with water, it is difficult to obtain a starting (meth)acryl group-containing isocyanate compound, and a durability and a mechanical strength of a polymer are poor.

In the aforesaid formula (1), $R^1$ is, independently of each other, an alkyl group having 1 to 6 carbon atoms, such as a methyl group, an ethyl group, a propyl group, a butyl group, a pentyl group and a hexyl group. Among these, a methyl group is preferable.

In the aforesaid formula (1), $R^2$ is, independently of each other, an alkylene group having 1 to 6 carbon atoms or a fluoroalkylene group having 1 to 6 carbon atoms. Examples of the alkylene group include a methylene group, an ethylene group, a propylene group, a butylene group, a pentylene group and a hexylene group. Examples of the fluoroalkylene group include 2,2-difluoroethylene, 3,3-difluoropropylene, 3,3,4,4-tetrafluorobutylene, 3,3,4,4,5,5-hexafluoropentylene and 3,3,4,4,5,5,6,6-octafluorohexylene. Among these, an ethylene group is preferable.

In the aforesaid formula (1), $R^3$ is an alkyl group having 1 to 4 carbon atoms, preferably a butyl group, and $R^4$ and $R^6$ are, independently of each other, a hydrogen atom or a methyl group.

The present method of the invention provides one kind of compound which is represented by the formula (1) and has one specific structure having each specific one value of m, n and k at a high ratio, as will described below. A high ratio means that an amount of the aforesaid one kind of compound having an each specific one value of m, n and k, based on a total amounts of the compound represented by the formula (1), is more than 95 mass %, preferably 97 mass % or more, further preferably 99 mass % or more. One kind of compound having one specific structure is particularly a compound having an each specific one value of m, n, k, $R^1$, $R^2$, $R^3$, $R^4$ and $R^6$ and a specific one kind of alkyleneoxide structure. In the present invention, the ratio is determined in gas chromatography, hereinafter referred to as "GC". The details of GC will be described below. When the compound is mixed with a non-silicone monomer such as 2-hydroxyethyl methacrylate, any turbidity does not occur and a transparent polymer is obtained, because the starting compound has a high ratio of one specific structure. If the ratio is less than 95 mass %, for instance, other compounds having different values of m are contained in an amount of more than 5 mass %, a mixture of the present silicone compound and a non-silicone monomer is turbid and does not provide a colorless and transparent polymer.

When m is 3, n is 1, k is 1, $R^1$ is a methyl group, $R^2$ is an ethylene group, $R^3$ is a butyl group, $R^4$ and $R^5$ are each a hydrogen atom and $R^6$ is a methyl group in the formula (1), the molecular weight is 997 and a content of siloxanes is approximately 46 mass %, based on the total mass of the compound other than the fluoromethyl group and a content of fluorine atoms is approximately 22 mass %, based on the total mass of the compound. That is, the compound comprises a large amount of Si atoms, whereby a polymer obtained therefrom has high oxygen permeability. Further, the compound has a desired amount of a fluorine atom and, therefore, anti-staining property of a polymer is improved.

The present invention further provides methods for preparing the afore-mentioned compound represented by the formula (1).

One of the present methods comprises a step of reacting a silicone compound represented by the following formula (2):

(2)

wherein m, n, $R^1$, $R^2$, $R^3$, $R^4$ and $R^5$ are as defined above; with a (meth)acryl group-containing isocyanate compound represented by the following formula (3):

(3)

wherein k and $R^6$ are as defined above.

The reaction is preferably carried out in such a manner that the (meth)acryl group-containing isocyanate compound represented by the formula (3) is slowly added to a solution of the polyorganosiloxane represented by the formula (2) in toluene or hexane to be allowed to react at a temperature of from 0 to 50 degrees C. under cooling, for instance, in a water bath.

The amount of the (meth)acryl group-containing isocyanate compound (3) is 1 to 3 moles, preferably 1.05 to 2 moles, per mole of the polyorganosiloxane represented by the formula (2). If the amount is smaller than the lower limit, the polyorganosiloxane (2) would remain unreacted in the reaction product and a high ratio of one specific structure of the formula (1) is not attained. If the amount is larger than the upper limit, this is economically disadvantageous.

The afore-mentioned reactions may be carried in the presence of a catalyst. Any catalyst generally used for isocyanate reactions may be used. Preferred are tin compound catalysts and amine catalysts. As the tin compound catalysts, a tin (II) salt of carboxylic acid, i.e. dioctyltin carboxylate, and dioctyltin oxide are preferred for its catalyst activity. As the amine catalysts, tertiary amines such as triethylamine, tributylamine and N-ethyldiisopropylamine are preferred. The amount of the catalyst may be 0.001 to 0.1 part by mass, preferably 0.005 to 0.05 part by mass, per 100 parts by mass of the component (2). If the amount is larger than the upper limit, the catalyst effect may saturate and this is not economically. If the amount is smaller than the lower limit, an enough catalyst effect is not attained, so that the reacting rate is slow and productivity is worse.

In the afore-mentioned reactions, a polymerization inhibitor may be added, if needed. Any conventional polymerization inhibitor for a (meth)acryl compound may be used, such as, for instance, a phenol type polymerization inhibitor such as hydroquinone, hydroquinone monomethyl ether, 2-tert-butyl hydroquinone, 4-methoxy phenol and 2,6-di-tert-butyl-4-methylphenol(BHT). These may be used singly or two or more of them may be used in combination. The amount is preferably 5 to 500 ppm, further preferably 10 to 100 ppm, based on an amount of compound to be obtained, but is not limited to these.

It is preferred that the unreacted silicone compound (2) is monitored in GC. After disappearance of its peak is confirmed, an alcohol, such as methanol or ethanol, is poured into the reaction mixture to inactivate the isocyanate group of the unreacted (meth)acryl group-containing isocyanate compound. Subsequently, an organic solvent and water are added to the mixture and stirred and, then, left standing to allow separation into an organic phase and an aqueous phase. The organic phase is washed several times with water and, then, a silicone compound (1) which has one specific structure is obtained at a high ratio by stripping off the solvent present in the organic phase because almost no side reaction occurs.

The silicone compound represented by the aforesaid formula (2) is prepared by an addition reaction of a polyorganohydrogen siloxane represented by the following formula (4):

wherein m, $R^1$, $R^2$ and $R^3$ are as defined above;
with a compound represented by the following formula (5), hereinafter referred to as "allyl ether compound":

wherein n, $R^4$ and $R^5$ are as defined above.

This addition reaction may be carried out in any conventional manners. For instance, the reaction is carried out in the presence of a hydrosilylation catalyst such as platinum group metal compounds. A solvent may be used. Examples of the solvent include aliphatic or aromatic solvents such as hexane, methylcyclohexane, ethylcyclohexane and toluene; and alcoholic solvents such as ethanol and IPA. A ratio of the aforesaid compounds to be used may be according to conventional manners. The amount of the allyl ether compound may be 1.2 moles or more, preferably 1.5 moles or more, per mole of the polyorganohydrogen siloxane. The upper limit of the amount may be usually 5 moles or less, particularly 3 moles or less, but is not limited to them.

The allyl ether compound represented by the aforesaid formula (5) is preferably represented by the following formulas.

It is preferred that the ally ether compound is optionally diluted with a solvent to which, then, a hydrosilylation catalyst of platinum family is added. Any conventional hydrosilylation catalysts of platinum family may be used and not limited to any particular one. Subsequently, the polyorganohydrogen siloxane is added dropwise to the mixture to react at room temperature or a higher temperature. After the completion of the addition, the reaction mixture is held under heating, until disappearance of the peak of the raw material, polyorganohydrogen siloxane, is confirmed, for instance, in GC. After the end point of the reaction is confirmed in GC, the unreacted polyorganohydrogen siloxane does not remain in a product, so that a silicone compound obtained has one specific structure at a higher ratio. The aforesaid addition reaction may be conducted in one step.

After the completion of the addition reaction, an excessive allyl ether compound is removed from the reaction liquid. For instance, the reaction liquid is subjected to stripping under a reduced pressure, or washed with ion exchanged water or an aqueous sodium sulfate solution to extract the allyl ether compound into an aqueous phase. Here, a proper amount of solvent, such as toluene and hexane, may preferably be used to attain clear phase separation. In particular, the solvent is stripped off from the organic phase under a reduced pressure, whereby the silicone compound represented by the aforesaid formula (2) and having a high ratio of one specific structure such as more than 95 mass %, even approximately 97 mass % or more, further approximately 99 mass % or more, is obtained. The silicone compound may be distilled twice or more to further increase the ratio. A high ratio means that an amount of the aforesaid one kind of compound having each specific one value of m and n, based on a total amounts of the compound represented by the formula (2), is more than 95 mass %, preferably 97 mass % or more, further preferably 99 mass % or more. The one specific structure means one kind of compound having each one value of m and n particularly, one kind of compound having each one value of m, n, $R^1$, $R^2$, $R^3$, and $R^4$ and one kind of alkylene oxide structure.

The polyorganohydrogen siloxane represented by the aforesaid formula (4) may be prepared in known manners. For instance, the compound (4) wherein m is 3, $R^1$ is a methyl group, $R^2$ is an ethylene group and $R^3$ is a butyl group may be prepared in the following manner. First, $BuMe(CF_3CH_2CH_2)$ SiOLi is synthesized using BuLi. 1,3,5-Tris(3,3,3-trifluoropropyl)-1,3,5-trimethylcyclo trisiloxane is subjected to a ring-opening reaction using the BuMe $(CF_3CH_2CH_2)$ SiOLi as an initiator and, then, the reaction is terminated with dimethylchlorosilane. Thus, a mixture of compounds having m of 2 to 5 is obtained. The mixture is distilled to collect a fraction at 146 degrees C. and 84 Pa to obtain a compound whose m is 3, at a ratio of 98 mass % or higher in the fraction obtained. Alternatively, the distillation may be carried out after the mixture is addition reacted with the allyl ether compound represented by the formula (5). However, the product of the addition reaction has a higher boiling point. Therefore, the former manner is preferred. Then, a silicone compound (2) having one specific structure is obtained at a higher ratio.

The silicone compound (2) may be prepared also by the steps of subjecting the allyl ether to a silylation to provide a silyl ester with a silylating agent such as hexamethyldisilazane, addition reacting the compound obtained in the aforesaid manners and, then, hydrolyzing the silyl ester.

The silicone compound of the present invention is well compatible with other compounds having a group polymerizable with the silicone compounds, such as compounds having a (meth)acryl group, hereinafter referred to as "polymerizable monomer". Therefore, the silicone compound copolymerizes with the polymerizable monomer to provide a colorless and transparent polymer. In particular, the silicone compound is well compatible with a fluorinated substituent group-containing (meth)acryl monomer, so that hydrophilicity and anti-staining property of the polymer obtained are increased.

Examples of the polymerizable monomer include acryl monomers such as (meth)acrylic acid, methyl (meth)acrylate, ethyl (meth)acrylate, (poly)ethylene glycol dimethacrylate, polyalkylene glycol mono(meth)acrylate, polyalkylene glycol monoalkyl ether (meth)acrylate, trifluoroethyl (meth)acrylate, 2-hydroxyethyl (meth)acrylate, and 2,3-dihydroxypropyl (meth)acrylate; acrylic acid derivatives such as N, N-dimethyl acrylamide, N, N-diethyl acrylamide, N-acryloyl morpholine, and N-methyl (meth)acrylamide; other ethylenically unsaturated aliphatic or aromatic compound such as crotonic acid, cinnamic acid, and vinyl benzoic acid; and silicone compounds having polymerizable groups such as a (meth)acryl group. These may be used singly or two or more of them may be used in combination.

The copolymerization of the present compound and the other polymerizable monomer mentioned just above may be carried out in conventional known manners. For instance, known polymerization initiator such as thermal polymerization initiators or photo polymerization initiators may be used. Examples of the polymerization initiator include 2-hydroxy- 2-methyl-1-phenyl-propane-1-one, azobis isobutyronitrile, azobis dimethylvaleronitrile, benzoyl peroxide, tert-butyl hydroperoxide, and cumene hydroperoxide. The polymerization initiator may be used singly or two or more of them may be used in combination. The amount of the polymerization initiator is 0.001 to 2 parts by mass, preferably 0.01 to 1 part by mass, relative to 100 parts by mass of a total amount of the polymerizable components.

A polymer having a unit derived from the compound in the present invention has high oxygen permeability and excellent hydrophilicity, anti-staining property and durability of mechanical strength in a phosphate buffer solution. Therefore, the present compounds are suitable as materials for preparing ophthalmic devices such as contact lenses, intraocular lenses and artificial corneas. A method for preparation of the ophthalmic device with the present polymer may be any conventional ones. For instance, a machining method and a molding method may be used for forming lenses such as contact lenses and intraocular lenses.

EXAMPLES

The present invention will be explained below in further detail with reference to a series of the Examples and the Comparative Examples, though the present invention is in no way limited by these Examples.

In the following descriptions, a viscosity was determined by a Cannon-Fenske viscosimeter and a specific gravity was as determined by a hydrometer. A refraction index was as determined by a digital refractometer RX-5000, ex Atago Co., Ltd. $^1$H-NMR analysis was conducted by JNM-ECP500, ex JEOL Ltd. with deuterochloroform as a measuring solvent. A ratio of a compound was determined by gas chromatography, i.e. GC. Conditions in GC were as follows.
[GC Conditions]
Gas chromatograph: ex Agilent Technologies, Inc.
Detector: FID, temperature of 300 degrees C.
Capillary Column: HP-5MS (0.25 mm×30 m×0.25 micrometer), ex J & W
Temperature rise program: 50 degrees C. for 5 minutes, 10 degrees C./minute and, then, maintained at 250 degrees C.
Temperature at an inlet: 250 degrees C.
Carrier gas: Helium with a flow rate of 1.0 ml/minute
Split ratio: 50:1
Injection volume: 1 microliter Synthesis Example 1

In a three-liter flask equipped with a stirring device, a dimroth condenser, a thermometer and a dropping funnel, put were 112.4 g (0.24 mol) of 1,3,5-tris(3,3,3-trifluoropropyl)-1,3,5-trimethylcyclo trisiloxane and 60 g of toluene, and cooled to an internal temperature of 0 degrees C. Then, 450 ml (0.72 mol) of a 1.6 M solution of n-butyllithium was added dropwise in the flask over two hours at the internal temperature of 0 to 15 degrees C. The reaction mixture was held at 15 degrees C. for one hour, to which a mixture of 337.4 g (0.72 mol) of 1,3,5-tris(3,3,3-trifluoropropyl)-1,3,5-trimethylcyclo trisiloxane and 270 g of tetrahydrofuran was then added dropwise over two hours at the internal temperature of 0 to 5 degrees C. The reaction mixture was aged at the internal temperature of 0 to 5 degrees C. for two hours and, then further at the internal temperature of 20 to 25 degrees C. for one hour. 7.3 g (0.72 mol) of triethylamine was added to the reaction mixture and, then, 88.6 g (0.94 mol) of dimethyldichlorosilane was added dropwise in the flask over two hours at the internal temperature of 20 to 25 degrees C. The reaction mixture was aged at the internal temperature of 20 to 25 degrees C. for one hour. 1000 Grams of water were added to the reaction mixture, stirred for 5 minutes and, then, left standing to cause phase separation. The aqueous phase was discarded. The solvent in the organic phase was distilled off under a reduced pressure to obtain 526 g of a mixture comprising 57.1% of the desired compound. The mixture was distilled to collect a fraction at 146 degrees C. and 84 Pa to obtain 255 g of a product with a yield of 47.8% (0.34 mol). $^1$H-NMR analysis showed that the product was a compound represented by the following formula (6). The ratio of the compound represented by the following formula (6) in the obtained product was 98.4 mass %, as determined in GC, the viscosity was 11 mm$^2$/s at 25 degrees C., the specific gravity was 1.144 at 25 degrees C. and the refraction index was 1.3810.

(6)

Example 1

In a one-liter flask equipped with a stirring device, a dimroth condenser, a thermometer and a dropping funnel, put were 38.25 g (0.375 mol) of ethylene glycol monoallyl ether represented by the following formula (7) and 100 g of toluene, and heated to 70 degrees C. 0.38 Gram of a solution of a catalyst, complex of alkali-neutralized chloroplatinic acid with vinyl siloxane, in toluene, containing 0.5% of platinum, was added in the flask. Then, 185 g (0.25 mol) of the compound represented by the aforesaid formula (6) was added dropwise in the flask with the dropping funnel over one hour. The reaction mixture was held at 100 degrees C. for one hour and, then, analyzed in GC. The peak of the compound represented by the aforesaid formula (6) disappeared, which means that the reaction completed. 100 Grams of ion exchanged water were added to the reaction mixture with stirring to wash it and, then, left standing to cause phase separation. The aqueous phase containing the excessive ethylene glycol monoallyl ether was removed. The organic phase was similarly washed twice with each 100 g of ion exchanged water and, then, the toluene in the organic phase was stripped off under a reduced pressure to obtain 193.7 g (0.23 mol) of a colorless and transparent liquid, silicone compound represented by the following formula (8). The yield was 92%. The ratio of the silicone compound represented by the following formula (8) in the obtained product was 98.1 mass %, as determined in GC.

(7)

(8)

In a one-liter flask equipped with a stirring device, a dimroth condenser, a thermometer and a dropping funnel, put were 210.5 g (0.25 mol) of the silicone compound represented by the formula (8), 0.02 g (0.01 mass %) of dioctyl tin oxide, 0.01 g of Ionol, i.e. 2,6-di-tert-butyl-4-methylphenol, ex Japan Chemtech Co. Ltd., and 0.01 g of 4-methoxyphenol to prepare a mixture. 40.3 Grams (0.26 mol) of a methacryl group-containing isocyanate compound represented by the following formula (9) was added dropwise to the mixture over one hour. The internal temperature rose from 20 degrees C. up to 40 degrees C. The mixture was held at 40 degrees C., while monitoring the peak of the silicone compound represented by the formula (8) in GC. Four hours later, the intensity of the peak of the silicone compound fell down below the detection limit by GC and, then, 4.0 g (0.125 mol) of methanol was added to the reaction mixture. Further, 180 g of hexane and 180 g of ion exchanged water were added to the reaction mixture to wash it. The reaction mixture was left standing to cause phase separation. The aqueous phase was removed and, subsequently, the organic phase was washed twice with ion exchanged water. The solvent, hexane, was stripped off from the organic phase under a reduced pressure to obtain 204.3 g of a colorless and transparent liquid product. $^1$H-NMR analysis showed that the obtained compound in the product was a silicone compound represented by the following formula (10), hereinafter referred to as silicone compound 1. The yield was 82% and the aforesaid amount (204.3 g) was 0.20 mol. The ratio of the silicone compound represented by the following formula (10) in the product was 97.1 mass %, as determined in GC, the viscosity was 112.9 mm$^2$/s at 25 degrees C., the specific gravity was 1.165 at 25 degrees C. and the refraction index was 1.4131.

Example 2

The procedures of Example 1 were repeated, except that 51.7 g (0.26 mol) of a methacryl group-containing isocyanate compound represented by the following formula (11) was used in place of the methacryl group-containing isocyanate compound represented by the formula (9). 205.5 Grams of a colorless and transparent liquid product was obtained. $^1$H-NMR analysis showed that the obtained compound in the product was a silicone compound represented by the following formula (12), hereinafter referred to as silicone compound 2. The yield was 79% and the aforesaid amount (205.5 g) was 0.19 mol. The ratio of the silicone compound represented by the following formula (12) in the product was 97.0 mass %, as determined in GC, the viscosity was 98.7 mm$^2$/s at 25 degrees C., the specific gravity was 1.116 at 25 degrees C. and the refraction index was 1.4155.

(11)

(12)

Comparative Synthesis Example 2

The procedures of Example 9 described in Japanese Patent Application Laid-Open No. 2008-274278, Patent Literature 8, were repeated to synthesize a polysiloxane represented by the following formula (13). The obtained product was a mixture of a compound whose m was 0, a compound whose m was 3, a compound whose m was 6, and a compound whose m was 9, hereinafter referred to as silicone compound 3.

(9)

(10)

(13)

(15)

Preparation of a Monomer Mixture

Example 3

60 Parts by mass of silicone compound 1 prepared in Example 1, 35 parts by mass of N, N-dimethyl acryl amide, 1 part by mass of triethylene glycol dimethacrylate, 5 parts by mass of trifluoroethyl methacrylate and 0.5 part by mass of DAROCUR 1173, ex Ciba Specialty Chemicals Inc., were mixed with stirring to obtain monomer mixture 1.

Example 4

In Example 4, the same components and the same manners as in Example 3 were used, except that silicone compound 2 prepared in Example 2 was used instead of silicone compound 1 to obtain a monomer mixture, hereinafter referred to as monomer mixture 2.

Example 5

60 Parts by mass of silicone compound 1 prepared in Example 1, 40 parts by mass of N, N-dimethyl acryl amide, 1 part by mass of triethylene glycol dimethacrylate and 0.5 part by mass of DAROCUR 1173, ex Ciba Specialty Chemicals Inc., were mixed with stirring to obtain monomer mixture 3.

Comparative Synthesis Example 3

The procedures of Example 1 described in Japanese Patent No. 4646152, Patent Literature 6, were repeated to synthesize a compound represented by the following formula (14), hereinafter referred to as silicone compound 4.

(14)

The obtained compound was a colorless and transparent liquid. The ratio of the silicone compound represented by the aforesaid formula (14) in the obtained product was 98.3 mass %, as determined in GC.

Comparative Synthesis Example 4

In a one-liter flask equipped with a stirring device, a dimroth condenser, a thermometer and a dropping funnel, put were 40.3 g (0.32 mol) of allyl methacrylate and 100 g of metylcyclohexane, and heated to 70 degrees C. 0.15 Gram of a solution of a catalyst, complex of alkali-neutralized chloroplatinic acid with vinyl siloxane, in toluene, containing 0.5% of platinum, was added in the flask. Then, 148 g (0.2 mol) of the compound represented by the aforesaid formula (6) was added dropwise in the flask with the dropping funnel over one hour. The reaction mixture was held at 100 degrees C. for one hour and, then, analyzed in GC. The peak of the compound represented by the aforesaid formula (6) disappeared, which means that the reaction completed. Metylcyclohexane was stripped off under a reduced pressure to obtain 165.3 g (0.194 mol) of a colorless and transparent liquid with a yield of 97%. $^1$H-NMR analysis showed that the obtained compound in the product was a silicone compound represented by the following formula (15). The ratio of the silicone compound represented by the formula (15) in the obtained product was 98.7 mass %, as determined in GC, the viscosity was 18.4 mm$^2$/s at 25 degrees C., the specific gravity was 1.143 at 25 degrees C. and the refraction index was 1.4046.

Comparative Examples 1 to 3

In Comparative Example 1, the same components and the same manners as in Example 3 were used, except that silicone compound 3 prepared in Comparative Synthesis Example 2 was used instead of silicone compound 1 to obtain a monomer mixture, hereinafter referred to as monomer mixture 4.

In Comparative Example 2, the same components and the same manners as in Example 3 were used, except that silicone compound 4 prepared in Comparative Synthesis Example 3 was used instead of silicone compound 1 to obtain a monomer mixture, hereinafter referred to as monomer mixture 5.

In Comparative Example 3, the same components and the same manners as in Example 3 were used, except that silicone compound 5 prepared in Comparative Synthesis Example 4, was used instead of silicone compound 1 to obtain a monomer mixture, hereinafter referred to as monomer mixture 6.

[Evaluations]
(1) Compatibility with Other Polymerizable Monomers

The appearances of the monomer mixtures obtained were observed visually. A mixture comprising a silicone compound having good compatibility with the other (meth)acryl compounds was colorless and transparent. In contrast, a mixture comprising a silicone compound having bad compatibility with the other (meth)acryl compounds was turbid. The results are as shown in Table 1.

(2) Appearance of a Film, Composed of the Polymer

The each mixture was deaerated in an argon atmosphere. The mixture obtained was poured into a mold having two pieces of quartz glass plates which faced each other. The mixture was irradiated with light from an extra high pressure mercury lamp for one hour to obtain a film having a thickness of approximately 0.3 mm. The appearance of the film was observed visually. The results are as shown in Table 1.

(3) Water Wettability, or Hydrophilicity, of a Film Surface, Composed of the Polymer Water contact angles of the films prepared in (2) above were determined by a liquid drop method with a contact angle meter CA-D type, ex Kyowa Interface Science Co., LTD. The results are as shown in Table 1.

(4) Anti-Staining Property of a Film, Composed of the Polymer

Two films for each one mixture were prepared in the same manner as in (2) above. One of the twos was soaked in a phosphate buffer solution, PBS(−), at 37 degrees C. for 24 hours. The film after soaked and another film without being soaked were stored in a well-known artificial lipid solution at 37 plus − minus 2 degrees C. for 8 hours. Then, the films were washed with PBS(−) and, subsequently, soaked in a 0.1% solution of sudan black sesame oil. When the colors were not different between the film after soaked and the film without being soaked, the film was evaluated as "good". When the color of the film after soaked was different from the film without being soaked, that is, the film was stained with the sudan black sesame oil, the film was evaluated as "bad". The results are as shown in Table 1.

(5) Durability of Mechanical Strength of a Film, Composed of the Polymer

Two films for each one mixture were prepared in the same manner as in (2) above. Any water on the surface of the films was wiped off. Then, one of the twos was soaked in a phosphate buffer solution, PBS(−), at 37 degrees C. for 24 hours. The film after soaked and another film without being soaked were cut into test samples having a dumbbell shape of a width of 2.0 mm. The top and the bottom of the test sample was held by a jig and pulled at a constant speed. Tensile strength and elongation at break were determined with a tensile tester AGS-50NJ, ex Shimadzu Corporation. When a change of the value of the tensile strength or the rupture elongation of the film after soaked, relative to the value of the film without being soaked was not larger than 10%, it was evaluated as "good". When a change of the value of the tensile strength or the rupture elongation of the film after soaked, relative to the value of the film without being soaked was larger than 10%, it was evaluated as "bad". The results are as shown in Table 1.

The compounds used in Comparative Examples 1 and 3 were less compatible with the other (meth)acryl monomers and did not provide a colorless and transparent polymer. Further, the polymers obtained from the monomer mixtures in Comparative Examples 1 to 3 had poor water wettability (hydrophilicity) and anti-staining property and the mechanical strength deteriorated in the phosphate buffer solution. In contrast, the silicone compound of the present invention is well compatible with the other (meth)acryl monomer and provides a colorless and transparent polymer. Further, the silicone compound is well compatible with a fluorinated (meth)acryl monomer, too. Therefore, the silicone compound provides a polymer having excellent water wettability and anti-staining property and the mechanical strength does not deteriorate in the phosphate buffer solution. Further, as shown in Example 5 of Table 1, the present silicone compound provides, on account of its fluorinated hydrocarbon group, a polymer having an excellent anti-staining property without other fluorinated monomer.

INDUSTRIAL APPLICABILITY

The present silicone compound provides a colorless and transparent polymer having a higher oxygen permeability, excellent hydrophilicity, anti-staining property and mechanical strength. Further, the present method provides a compound having one specific structure at a high ratio. Further the mechanical strength of the polymer obtained does not deteriorate in a phosphate buffer solution and the durability of mechanical strength is excellent. Accordingly, the present compound and the present method are useful for preparing ophthalmic devices such as contact lenses, intraocular lenses and artificial corneas.

TABLE 1

| | Example 3 | Example 4 | Example 5 | Comparative Example 1 | Comparative Example 2 | Comparative Example 3 |
|---|---|---|---|---|---|---|
| Monomer mixture | 1 | 2 | 3 | 4 | 5 | 6 |
| (1) Compatibility | Colorless and transparent | Colorless and transparent | Colorless and transparent | Turbid | Slightly turbid | Slightly turbid |
| (2) Appearance of the film | Colorless and transparent | Colorless and transparent | Colorless and transparent | Cloudy | Slightly cloudy | Slightly cloudy |
| (3) Water contact angle, ° | 47 | 46 | 45 | 59 | 64 | 53 |
| (4) Anti-staining property | Good | Good | Good | Bad | Bad | Bad |
| (5) Durability of mechanical strength | Good | Good | Good | Bad | Bad | Bad |

The invention claimed is:

1. A compound represented by the following formula (1):

2. The compound according to claim 1, wherein an amount of one kind of compound having each one value of m, n and k in the formula (1) is more than 95 mass % of a total mass of the compound.

3. The compound according to claim 2, wherein m in the formula (1) is 3.

4. A polymer having repeating units derived from the compound according to claim 3 and repeating units derived from at least one other compound having a group which is polymerizable with said compound.

5. An ophthalmic device composed of the polymer according to claim 4.

6. A polymer having repeating units derived from the compound according to claim 2 and repeating units derived from at least one other compound having a group which is polymerizable with said compound.

7. An ophthalmic device composed of the polymer according to claim 6.

8. The compound according to claim 1, wherein m in the formula (1) is 3.

9. A polymer having repeating units derived from the compound according to claim 8 and repeating units derived from at least one other compound having a group which is polymerizable with said compound.

10. An ophthalmic device composed of the polymer according to claim 9.

11. A polymer having repeating units derived from the compound according to claim 1 and repeating units derived from at least one other compound having a group which is polymerizable with said compound.

12. An ophthalmic device composed of the polymer according to claim 11.

13. A method for preparing a compound represented by the following formula (1):

wherein m is an integer of from 2 to 10, n is an integer of from 1 to 3, k is an integer of 1 or 2, $R^1$ is, independently of each other, an alkyl group having 1 to 6 carbon atoms, $R^2$ is, independently of each other, an alkylene group having 1 to 6 carbon atoms or a fluoroalkylene group having 1 to 6 carbon atoms, $R^3$ is an alkyl group having 1 to 4 carbon atoms, and $R^4$, $R^5$ and $R^6$ are, independently of each other, a hydrogen atom or a methyl group, comprising a step of reacting a silicone compound represented by the following formula (2):

wherein m, n, $R^1$, $R^2$, $R^3$, $R^4$ and $R^5$ are as defined above; with a (meth)acryl group-containing isocyanate compound represented by the following formula (3):

wherein k and $R^6$ are as defined above.

14. The method according to claim 13, wherein an amount of one kind of compound having each one value of m, n and k in the formula (1) is more than 95 mass % of a total mass of the compound.

15. The method according to claim 14, wherein m in the formula (1) is 3.

16. The method according to claim 13, wherein m in the formula (1) is 3.

* * * * *